United States Patent [19]

Cragoe, Jr. et al.

[11] 4,067,980

[45] Jan. 10, 1978

[54] SPIROBENZOXAZINIUM SALTS, METHOD OF USE AND COMPOSITIONS THEREOF AS ANTIHYPERTENSIVE AGENTS

[75] Inventors: Edward J. Cragoe, Jr., Lansdale; Gerald E. Stokker, Gwynedd Valley; Everett M. Schultz, Ambler, all of Pa.

[73] Assignee: Merck & Co., Inc., Rahway, N.J.

[21] Appl. No.: 714,465

[22] Filed: Aug. 16, 1976

[51] Int. Cl.[2] .................. A61K 31/535; C07D 265/12; C07D 498/10

[52] U.S. Cl. ........................... 424/248.4; 424/248.54; 424/248.55; 424/248.57; 544/71

[58] Field of Search ................ 260/244 R; 424/248.4, 424/248.54, 248.55, 248.57

[56] References Cited

PUBLICATIONS

McDonagh et al. J. Org. Chem. 33 (1) pp. 1-8 (1968).

*Primary Examiner*—Jane S. Myers
*Attorney, Agent, or Firm*—Michael C. Sudol, Jr.

[57] ABSTRACT

Quaternary salts of 3,4-dihydrospiro-2H-1,3-benzoxazines are prepared by treating 3,4-dihydrospiro-2H-1,3-benzoxazines with an alkylating agent. The products are antihypertensive agents.

10 Claims, No Drawings

SPIROBENZOXAZINIUM SALTS, METHOD OF USE AND COMPOSITIONS THEREOF AS ANTIHYPERTENSIVE AGENTS

This invention is concerned with novel quaternary salts of 3,4-dihydrospiro-2H-1,3-benzoxazines having therapeutic utility, processes for their preparation, methods of treating hypertension and novel pharmaceutical formulations comprising at least one of the novel compounds as active ingredient.

One embodiment of this invention is particularly concerned with the novel compounds of structural formula:

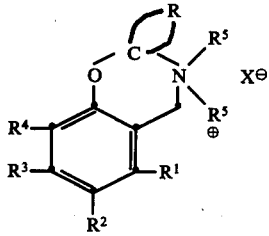

(I)

wherein
$R^1$ is hydrogen, methyl, chloro, or methoxy;
$R^2$ is halo, such as chloro, bromo, or iodo;
 lower alkyl, especially $C_{1-5}$ alkyl, either straight or branched chain, such as methyl, propyl, isopropyl, butyl, t-butyl, sec-butyl, pentyl or isopentyl;
$R^3$ is hydrogen;
 lower alkyl, especially $C_{1-7}$ alkyl, either straight or branched chain;
 lower alkoxy, especially $C_{1-5}$ alkoxy, either straight or branched chain such as methoxy;
 ethoxy, propoxy, butoxy or pentoxy, or halo, such as fluoro, chloro, bromo, or iodo;
$R^4$ is halo, such as chloro, bromo or iodo;
 lower alkyl, especially $C_{1-7}$ alkyl, either straight or branched chain;
 trifluoromethyl;
$R^5$ is lower alkyl either branched or straight chained having from 1 to 5 carbon atoms;

is 1. a spiro-carbocycle of 5 or 6 members, either unsubstituted or substituted with
 a. lower alkyl, especially $C_{1-5}$ alkyl,
 b. lower alkoxycarbonylalkyl, especially $C_{3-5}$ alkoxycarbonylalkyl;
 c. aryloxycarbonylalkyl having up to 10 carbon atoms such as benzyloxycarbonylmethyl;
2. a 6-membered spiro-heterocycle containing 1 hetero atom selected from oxygen or nitrogen such as spiro-tetrahydropyran, spiro-piperidine, wherein the nitrogen heteroatom can be substituted with lower alkanoyl, especially $C_{2-5}$ alkanoyl;
X is halo such as chloro, bromo or iodo;
 lower alkanoyloxy especially $C_{2-5}$ alkanoyloxy such as acetate.

A preferred aspect of the novel compounds of this invention are those of Formula I, wherein $R^1$ and $R^3$ are both hydrogen.

A more preferred aspect of the novel compounds of this invention are those of Formula I, wherein $R^1$ and $R^3$ are hydrogen, $R^2$ is $C_{1-5}$ alkyl, and $R^4$ is halo.

An even more preferred aspect of the novel compounds of this invention are those of Formula I, wherein $R^1$ and $R^3$ are hydrogen, $R^2$ is $C_{1-5}$ alkyl, particularly branched alkyl such as t-butyl, $R^4$ is halo, $R^5$ is methyl and

is spiro-cyclohexane and $X^-$ is iodo or acetate.

Another embodiment of this invention is the process for the preparation of the novel compounds of Formula I which is represented by:

REACTION SCHEME I

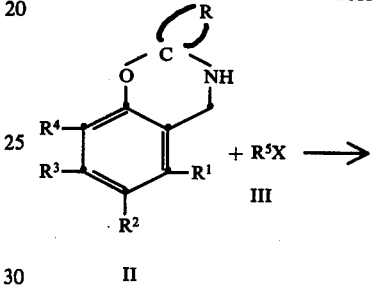

II

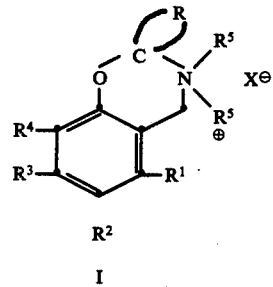

I

This novel process comprises mixing 3,4-dihydrospiro-2H-1,3-benzoxazines of Formula II and an alkylating agent of Formula III in an inert organic solvent generally an aprotic solvent such as benzene, dioxan, tetrahydrofuran, dimethyl formamide, or the like.

Generally an excess of the alkylating agent (Formula III) is used, preferably in more than a 2 to 1 mole ratio between the alkylating agent III to the starting benzoxazine (II).

The reaction is generally run at temperatures of 20°-110° C. but preferably at room temperature. Also the reaction is generally run to completion which is anywhere from 1 to 24 hours.

It is sometimes advantageous to perform the reaction in the presence of a weak base such as sodium bicarbonate. The amount of base is not critical but it is generally preferred to use one equivalent.

Generally the product (I) precipitates from the reaction mixture and can be isolated by filtration and washed with water to remove any inorganic salts.

If the product (I) does not precipitate one can isolate it by dilution of the reaction mixture with diethyl ether, at which time the product precipitates followed by filtering and washing the product. It should be noted that this process affords salts wherein the anion $X^-$ is halide. Conversion to products of formula I in which X⁻ is alkanoyloxy is readily accomplished via ion exchange resins.

The 3,4-dihydrospiro-2H-1,3-benzoxazines of Structure II, used as starting materials in the novel process of this invention are generally known compounds and readily prepared by processes described in Reaction Scheme II:

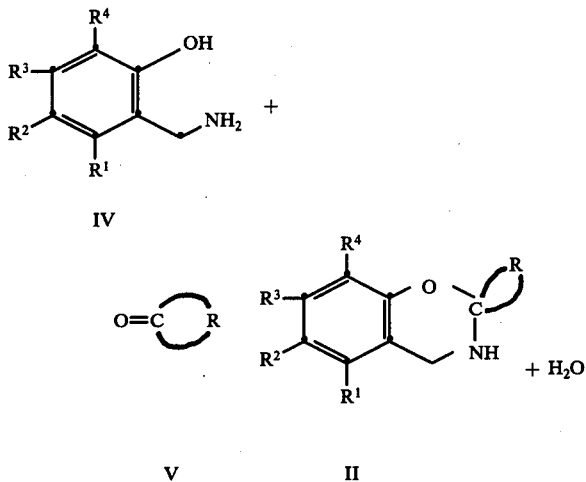

This novel process comprises mixing approximately equimolar amounts of an o-hydroxybenzylamine of Formula IV and a cyclic ketone of Formula v in an inert organic solvent such as benzene, dioxan, tetrahydrofuran, or the like, and warming the reaction mixture to temperatures of from 20°-110° C. or reflux temperature.

It is sometimes advantageous to perform the condensation reaction in the presence of an acid catalyst such as a sulfonic acid such as p-toluenesulfonic acid or methanesulfonic acid, or a $C_{1-5}$ alkanoic acid, preferably acetic acid. The amount of acid is not critical but it is preferred to use only a catalytic amount.

It is also sometimes advantageous to remove the water produced during the condensation from the reaction environment by having present an otherwise inert dehydrating agent such as molecular sieves, sodium sulfate, magnesium sulfate, or the like, or by refluxing the mixture under a Dean-Stark water trap where the solvent forms an azeotrope with water. Isolation of the product from the reaction mixture is performed by routine techniques well within the skill of one skilled in the art. Generally, the mixture is washed with a dilute base if an acid catalyst has been used. This is followed by a water wash, drying, evaporation of the solvent, and recrystallization from a solvent such as ethanol. If no acid catalyst is used, the reaction mixture is evaporated to dryness directly and the residue is purified by crystallization.

The o-hydroxybenzylamines of Structure IV, used as starting materials in the novel process of this invention, are generally known compounds and readily prepared by processes described in the literature such as U.S. Pat. Nos. 3,794,734; 3,809,721; 3864,401; and Great Britain Pat. No. 1,374,294.

Further embodiments of this invention are the novel pharmaceutical compositions comprising the quaternary salts of the spirobenzoxazines as active ingredient, and the novel methods of treating hypertension with the pharmaceutical compositions.

Pharmacological studies employing rats as the experimental animals indicate that the instant products and compositions containing the active products are effective antihypertensive agents which can be used in the treatment of conditions associated with elevated blood pressure.

The compositions containing the spirobenzoxazinium salts of this invention as the active ingredient for use as antihypertensive agents can be administered in a wide variety of therapeutic dosage forms in conventional vehicles for sytemic administration as, for example, by oral administration in the form of tablets, capsules, solutions, or suspensions, or by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kg. of body weight per day. These dosages are well below the toxic or lethal dose of the products. Capsules containing the products of this invention can be prepared by mixing a spirobenzoxazinium salt of this invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch, or magnesium stearate. The liquid forms in which the active ingredients may be incorporated include suitably flavored suspending or dispersing agents such as the synthetic and natural gums, for example, tragacanth, acacia, methylcellulose and the like. Other dispersing agents which may be employed include glycerin and the like. For parenteral administration sterile suspensions and solutions are desired. Isotonic preparations which generally contain suitable preservative are employed when intravenous administration is desired.

EXAMPLE 1

3,3-Dimethyl-3,4-dihydro-6-(1,1-dimethylethyl)-8-iodospiro-[2H-1,3-benzoxazinium-2,1'-cyclohexane]iodide Sodium bicarbonate (0.84 g., 0.01 mole) is added to a solution of 3,4-dihydro-6-(1,1-dimethylethyl)-8-iodospiro[2H-1,3-benzoxazine-2,1'-cyclohexane] (7.68 g., 0.02 mole) in dimethylformamide (100 ml.) immediately followed by methyl iodide (20 ml.) (large excess). The mixture is stirred at room temperature for 16 hours, diluted with diethyl ether (200 ml.), filtered and the crystals are washed with water. Yield: 8.6 g. (0.0159 mole, 79.5%), m.p. 199°-200° C (dec). Crystallized from ethanol-water (1:1) m.p. 199°-200° (dec).

Calc.: C, 42.16; H, 5.40; N, 2.59; Found: C, 42.15; H, 5.20; N, 2.55.

EXAMPLE 2

3,3-Dimethyl-3,4-dihydro-6-(1,1-dimethylethyl)-8-chlorospiro[2H-1,3-benzoxazinium-2,1'-cyclohexane]iodide By the process in Example 1 but using 3,4-dihydro-6-(1,1-dimethylethyl)-8-chlorospiro[2H-1,3-benzoxazine-2,1'-cyclohexane] (1.47 g., 0.005 mole) and crystallizing from ethanol-water (1:6) there is obtained 3,3-dimethyl-3,4-dihydro-6-(1,1-dimethylethyl)-8-chlorospiro[2H-

1,3-benzoxazinium-2,1'-cyclohexane]iodide (1.3 g.), m.p. 175°–176° (dec).

EXAMPLE 3

3,3,3',3',5',5'-Hexamethyl-3,4-dihydro-6-(1,1-dimethylethyl)-8-iodospiro[2H-1,3-benzoxazinium-2,1'-cyclohexane]iodide hemihydrate By the process in Example 1 but using 3',3',5',5'-tetramethyl-3,4-dihydro-6-(1,1-dimethylethyl)-8-iodospiro-[2H-1,3-benzoxazine-2,1'-cyclohexane] (2.2 g., 0.005 mole) and crystallizing from methanol-water (1:1) there is obtained 3,3,3',3',5',5'-hexamethyl-3,4-dihydro-6-(1,1-dimethylethyl)-8-iodospiro[2H-1,3-benzoxazinium-2,1'-cyclohexane]iodide hemihydrate (0.3 g.), m.p. 151°–152° (dec).

EXAMPLE 4

3,3-Dimethyl-3,4-dihydro-4',6-bis(1,1-dimethylethyl)-8-iodospiro[2H-1,3-benzoxazinium-2,1'-cyclohexane]iodide hemihydrate By the process in Example 1 but using 3,4-dihydro-4',6-bis(1,1-dimethylethyl)-8-iodospiro[2H-1,3-benzoxazine-2,1'-cyclohexane] (2.2 g., 0.005 mole) and crystallizing from ethanol-water (2:3) there is obtained 3,3-dimethyl-3,4-dihydro-4',6-bis(1,1-dimethylethyl)-8-iodospiro[2H-1,3-benzoxazinium-2,1'-cyclohexane]iodide hemihydrate (1.9 g.), m.p. 151°–153° (dec).

EXAMPLE 5

1'-Acetyl-3,3-dimethyl-3,4-dihydro-6-(1,1-dimethylethyl)-8-iodospiro[2H-1,3-benzoxazinium-2,4'-piperidine]iodide hemihydrate By the process in Example 1 but using 1'-acetyl-3,4-dihydro-6-(1,1-dimethylethyl)-8-iodospiro[2H-1,3-benzoxazine-2,4'-piperidine] (8 g., 0.018 mole) and crystallizing from ethanol-water (1:2) there is obtained 1'-acetyl-3,3-dimethyl-3,4-dihydro-6-(1,1-dimethylethyl)-8-iodospiro[2H-1,3-benzoxazinium-2,4'-piperidine]iodide hemihydrate (8 g.), m.p. 148°–150° (dec).

EXAMPLE 6

3,3-Dimethyl-3,4-dihydro-6-(1,1-dimethylethyl)-8-iodospiro-[2H-1,3-benzoxazinium-2,4'-piperidine]chloride hydrochloride hemihydrate The spirobenzoxazinium iodide (7.75 g., 0.013 mole) from Example 5 is dissolved in ethanol (40 ml), hydrochloric acid (12 N, 20 ml.) is added and the mixture is refluxed for 1½ hours. The mixture is then evaporated to dryness under reduced pressure. The residue is dissolved in water (50 ml.) and passed down a column of Dowex-1(Cl-). The first 150 ml. of solution that is collected is evaporated to dryness. The residue is crystallized from ethanolether (1:3) to obtain 3,3-dimethyl-3,4-dihydro-6-(1,1-dimethylethyl)-8-iodospiro[2H-1,3-benzoxazinium-2,4'-piperidine]chloride hydrochloride hemihydrate (4 g.), m.p. 163°–164° C. (dec).

EXAMPLE 7

3,3-Dimethyl-3,4-dihydro-6-(1,1-dimethylethyl)-8-iodospiro-[2H-1,3-benzoxazinium-2,1'-cyclohexane]-acetate hemihydrate The corresponding spirobenzoxazinium iodide (Example 1) (1.36 g., 0.0025 mole) is dissolved in 50% aqueous acetic acid (200 ml) and passed down a column of Dowex-1 × 2 acetate resin. The first 350 ml. that is collected is evaporated to dryness. The residue is crystallized from ethanolether (1:100) to obtain 3,3-dimethyl-3,4-dihydro-6-(1,1-dimethylethyl)-8-iodospiro[2H-1,3-benzoxazinium-2,1'-cyclohexane]acetate hemihydrate (0.8 g.), m.p. 159°–160° (dec).

EXAMPLE 8

3,3-Dimethyl-3,4-dihydro-6-(1,1-dimethylethyl)-8-iodospiro-[2H-1,3-benzoxazinium-2,1'-cyclopentane]iodide 2-Aminomethyl-4-(1,1-dimethylethyl)-6-iodophenol (1.5 g., 0.005 mole), cyclopentanone (0.5 g., 0.0059 mole) and benzene (50 ml.) are combined and refluxed under a water separator for 3 hours. The benzene is evaporated under reduced pressure and the residue dissolved in dry dimethylformamide (20 ml.). Sodium bicarbonate (0.42 g., 0.005 mole) and methyliodide (5 ml.) are added. The mixture is stirred at room temperature for 16 hours and then diluted with diethyl ether (200 ml.), filtered and the crystals are washed with water. Yield after crystallizing from ethanolether (1:5) is 0.6 g., m.p. 192.5°–193° (dec).

Calc.: C, 41.01; H, 5.16; N, 2.66; Found: C, 41.40; H, 5.42; N, 2.52.

EXAMPLE 9

The following spirobenzoxazinium iodides are prepared in a manner similar to Example 8 by using the appropriate aminomethylphenol and ketone as shown.

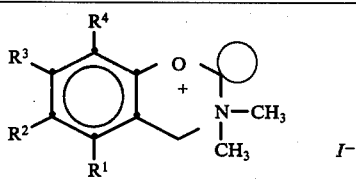

| Ex. | R⁴ | R³ | R² | R¹ | | m.p. |
|---|---|---|---|---|---|---|
| 9 | I | H | C(CH₃)₃ | H | 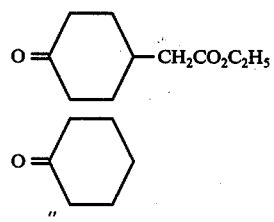 | 165–6° d |
| 10 | I | H | Cl | H | | 207–8° d |
| 11 | I | H | CH(CH₃)₂ | H | " | 174–5° d |
| 12 | " | " | C(CH₃)₂CH₂CH₃ | " | " | 205–6° d |

-continued

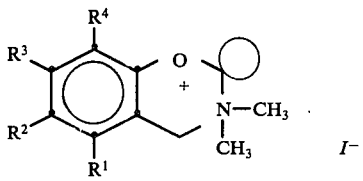

| Ex. | R⁴  | R³   | R²      | R¹   |    | m.p.     |
|-----|-----|------|---------|------|----|----------|
| 13  | H   | "    | C(CH₃)₃ | "    | "  | 172–3° d |
| 14  | CF₃ | "    | "       | "    | "  | 182–3° d |
| 15  | Cl  | C₂H₅ | Cl      | CH₃  | "  | 210–11° d |
| 16  | Cl  | OCH₃ | Cl      | OCH₃ | "  | 188–9° d |

EXAMPLE 17

1 Tablets - 10,000 scored tablets for oral use, each containing 500 mg. of active ingredient are prepared from the following ingredients:

|                                                                                                   | Gm. |
|---------------------------------------------------------------------------------------------------|-----|
| 3,3-Dimethyl-3,4-dihydro-6-(1,1-dimethyl-ethyl)-8-iodospiro[2H-1,3-benzoxazinium-2,1'-cyclohexane]acetate hemihydrate | 5000 |
| Starch, U.S.P                                                                                     | 350 |
| Talc, U.S.P.                                                                                      | 250 |
| Calcium stearate                                                                                  | 35  |

The active ingredient is granulated with a 4% w./v. aqueous solution of methylcellulose U.S.P. (1500 cps). To the dried granules is added a mixture of the remainder of the ingredients and the final mixture compressed into tablets of proper weight.

2. Capsules - 10,000 two-piece hard gelatin capsules for oral use, each containing 250 mg. of active ingredient are prepared from the following ingredients:

|                                                                                                   | Gm. |
|---------------------------------------------------------------------------------------------------|-----|
| 3,3-Dimethyl-3,4-dihydro-6-(1,1-dimethyl-ethyl)-8-iodospiro[2H-1,3-benzoxazinium-2,1'-cyclohexane]acetate hemihydrate | 2500 |
| Lactose, U.S.P.                                                                                   | 1000 |
| Starch, U.S.P.                                                                                    | 300 |
| Talc, U.S.P.                                                                                      | 65  |
| Calcium Stearate                                                                                  | 25  |

The active ingredient is mixed with the starch lactose mixture followed by the talc and calcium stearate. The final mixture is then encapsulated in the usual manner. Capsules containing 10, 25, 50, and 100 mg. of active ingredient are also prepared by substituting 100, 250, 500, and 1000 gm. of 2500 gm. in the above formulation

What is claimed is:

1. A compound of the formula:

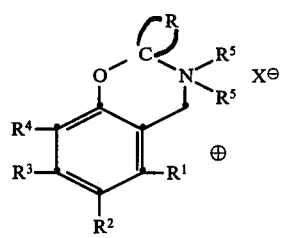

wherein
R¹ is hydrogen, methyl or methoxy;
R² is halo or lower alkyl;
R³ is hydrogen, lower alkyl or lower alkoxy;
R⁴ is halo, lower alkyl or trifluoromethyl;
R⁵ is lower alkyl;

is spiro-cyclohexane, spiro-cyclopentane spiro-4'-piperidine or spiro-4'-piperidine wherein the nitrogen heteroatom is substituted by lower alkanoyl and
X is halo or lower alkanoyloxy.

2. The compound of claim 1 with the formula:

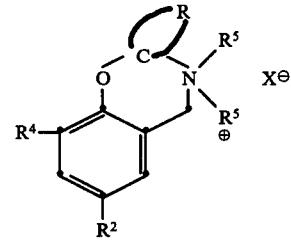

wherein R², R⁴, R⁵, X and

are as defined therein.

3. The compound of claim 1 with the formula:

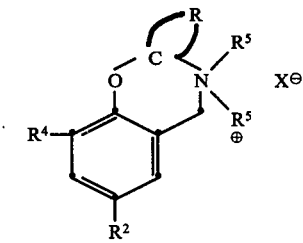

wherein R² is lower alkyl, R⁴ is halo, and R⁵, X and

are as defined therein.

4. The compound of claim 1 with the formula:

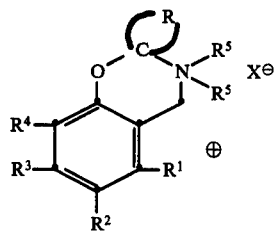

wherein $R^2$ is lower alkyl, $R^4$ is halo, $R^5$ is methyl, X is halo or acetoxy and

is defined therein.

5. The compound of claim 1 which is 3,3-dimethyl-3,4-dihydro-6-(1,1-dimethylethyl)-8-iodospiro[2H1,3-benzoxazinium-2,1'-cyclohexane]iodide.

6. The compound of claim 1 which is 3,3-dimethyl-3,4-dihydro-6-(1,1-dimethylethyl)-8-iodospiro[2H-1,3-benzoxazinium-2,1'-cyclohexane]acetate.

7. The compound of claim 1 which is 1'-acetyl-3,3-dimethyl-3,4-dihydro-6-(1,1-dimethylethyl)-8-iodospiro[2H-1,3-benzoxazinium-2,4'-piperidine]iodide.

8. The compound of claim 1 which is 3,3-dimethyl-3,4-dihydro-6-(1,1-dimethylpropyl)-8-iodospiro[2H-1,3-benzoxazinium-2,1'-cyclohexane]iodide.

9. A method of treating hypertension which comprises administration to a patient in need of such treatment a therapeutically effective amount of a compound of the formula:

wherein
$R^1$ is hydrogen, methyl or methoxy,
$R^2$ is halo or lower alkyl;
$R^3$ is hydrogen, lower alkyl or lower alkoxy;
$R^4$ is halo, lower alkyl or trifluoromethyl;
$R^5$ is lower alkyl;

is spiro-cyclohexane, spiro-cyclopentane spiro-4'piperidine or spiro-4'-piperidine wherein the nitrogen heteroatom is substituted by lower alkanoyl and X is halo or lower alkanoyloxy.

10. A pharmaceutical composition comprising a pharmaceutically acceptable carrier and a therapeutically effective amount of a compound of the formula for use in treating hypertension:

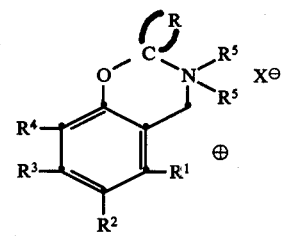

wherein
$R^1$ is hydrogen, methyl or methoxy;
$R^2$ is halo or lower alkyl;
$R^3$ is hydrogen, lower alkyl or lower alkoxy;
$R^4$ is halo, lower alkyl or trifluoromethyl;
$R^5$ is lower alkyl;

is spiro-cyclohexane, spiro-cyclopentane spiro-4'-piperidine or spiro-4'-piperidine wherein the nitrogen heteroatom is substituted by lower alkanoyl; and X is halo or lower alkanoyloxy.

* * * * *